United States Patent [19]

Curran et al.

[11] 4,085,110

[45] Apr. 18, 1978

[54] 1,2,3,5,6,7-HEXAHYDRODICYCLOPENTA[-b,e,]PYRIDINE DERIVATIVES

[75] Inventors: Adrian Charles Ward Curran, South Cave; Roger Crossley, Reading; David George Hill, Cookham, all of England

[73] Assignee: John Wyeth & Brother, Ltd., Taplow, England

[21] Appl. No.: 747,837

[22] Filed: Dec. 6, 1976

Related U.S. Application Data

[60] Division of Ser. No. 624,080, Oct. 20, 1975, Pat. No. 4,031,102, which is a continuation-in-part of Ser. No. 600,257, Jul. 30, 1975, which is a continuation-in-part of Ser. No. 460,265, Apr. 11, 1974, abandoned, which is a continuation-in-part of Ser. No. 403,289, Oct. 3, 1973, abandoned.

[30] Foreign Application Priority Data

| Oct. 21, 1972 | United Kingdom | 48595/72 |
| Oct. 15, 1973 | United Kingdom | 7424/73 |
| Jul. 21, 1973 | United Kingdom | 34866/73 |
| Aug. 16, 1973 | United Kingdom | 38701/73 |
| Oct. 17, 1973 | United Kingdom | 48595/73 |

[51] Int. Cl.² ............................................. C07D 221/06
[52] U.S. Cl. ....................... 260/294.8 B; 260/294.8 C; 424/263
[58] Field of Search ................................. 260/294.8 B

[56] References Cited

U.S. PATENT DOCUMENTS

3,733,331  5/1973  Hiltmann et al. ................. 260/295 K

FOREIGN PATENT DOCUMENTS

2,352,585  5/1974  Germany ........................... 260/287 T

OTHER PUBLICATIONS

Klingsberg, Pyridine and its Derivatives, Part Two, Interscience Pub., pp. 232–240, (1961).

*Primary Examiner*—Alan L. Rotman
*Attorney, Agent, or Firm*—Arthur E. Wilfond

[57] ABSTRACT

The invention relates to novel cyclopentena[b,e]pyridine derivatives which have a thioamide group in the 7-position. The compounds are anti-ulcer agents.

8 Claims, No Drawings

1,2,3,5,6,7-HEXAHYDRODICYCLOPENTA[b,e]-PYRIDINE DERIVATIVES

The invention relates to novel pyridine derivatives and to pharmaceutical compositions containing the novel derivatives. This application is a divisional of Ser. No. 624,080 filed Oct. 20, 1975, now Pat. No. 4,031,102 which in turn is a continuation-in-part of our co-pending application, Ser. No. 600,257 filed July 30, 1975 which is a continuation-in-part of our application Ser. No. 460,265 filed Apr. 11, 1974 now abandoned which in turn is a continuation-in-part of our Ser. No. 403,289 filed Oct. 3, 1973 abandoned.

The invention provides a compound of formula I

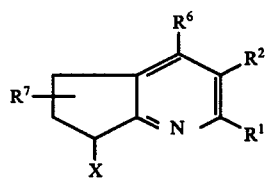

and acid addition salts thereof with pharmaceutically acceptable acids, wherein $R^1$, $R^2$ and $R^6$ are the same or different and are selected from hydrogen, alkyl of 1 to 6 carbon atoms, phenylalkyl wherein the alkyl group has 1 to 6 carbon atoms, or phenyl groups, or $R^1$ and $R^2$ taken together represet a polymethylene chain of 3,4 or 5 carbon atoms, $R^7$ represents hydrogen or 1 or 2 groups selected from alkyl groups of 1 to 6 carbon atoms, which may be substituted by alkoxy of 1 to 6 atoms or trifluoromethyl; phenylalkyl wherein the alkyl group has 1 to 6 carbon atoms and phenyl groups, and when $R^1$ and $R^2$ taken together from an alkylene chain the resulting ring may be substituted by from 1 to 3 $R^7$ groups as above defined, X is $CSNHR^3$ wherein $R^3$ is hydrogen or alkyl of 1 to 6 carbon atoms and any of the phenyl groups or the phenyl portion of any phenylalkyl groups $R^1$, $R^2$, $R^6$ and $R^7$ may be substituted by alkyl of 1 to 6 carbon atoms, alkoxy of 1 to 6 carbon atoms, halogen, nitro or trifluoromethyl with the provisos that (1) when $R^1$ and $R^2$ or $R^2$ and $R^6$ are both alkyl they are selected from normal and secondary alkyl groups and (2) when two alkyl groups $R^7$ are present on the same carbon atom then they are both n-alkyl groups and when two $R^7$ alkyl groups are present on adjacent carbon atoms they are selected from normal and secondary alkyl groups.

$R^7$ may be in the same position as X.

When any of $R^1$, $R^2$, $R^3$, $R^6$ or $R^7$ is an alkyl radical this is a lower alkyl radical which may have a straight or branched chain, having from 1 to 6 carbon atoms, e.g. methyl, ethyl, n-, and iso-propyl and n-, s- and t-butyl, $R^7$ may be a gem-dimethyl group and when a single radical may be on the same carbon atom as the $CSNHR^3$ group. The term alkyl radical is also intended to embrace cyclic alkyl radicals e.g. cyclobutyl, cyclopentyl and cyclohexyl. When any of $R^1$, $R^2$, $R^6$ or $R^7$ is a phenyl alkyl radical the alkyl portion may be as discussed above for an alkyl radical.

Particular preferred compounds are those in which one of $R^1$, $R^2$, $R^6$ and $R^7$ is methyl and the others are hydrogen Compounds wherein $R^3$ is selected from hydrogen and methyl are also preferred.

Thus, the present invention provides, in one preferred aspect, compounds of formula II

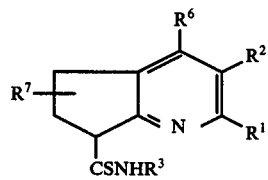

and pharmaceutically acceptable acid addition salts thereof, wherein one of $R^1$, $R^2$, $R^3$ and $R^6$ are selected from hydrogen and methyl.

The compounds of formula I can form acid addition salts with inorganic acids e.g. hydrochloric, hydrobromic, sulphuric or nitric acids, or organic acids e.g. fumaric, maleic, or tartaric acids. These acid addition salts are included in the invention.

In the compounds of formula I the carbon atom to which $CSNHR^3$ is attached is asymmetric. Consequently the compounds can exist in optically active d and l forms. These optically active forms and the recemates are included in the invention. The optically active forms may be separated by standard techniques either by formation of an acid salt with an optically active acid or by use of an optically active base with a precursor compound in which X is COOH and conversion of this to the desired isomer wherein X is $CSNHR^3$.

Compounds of formula I, wherein X is $CSNHR^3$ are anti-ulcer agents which have anti-ulcer activity determined by the method of Brodie and Hanson, J. Applied Physiology, 15, 291, 1960 or anti-secretory activity as determined by the test mentioned below.

Compounds of formula I, wherein X is $CSNHR^3$ often display antisecretory activity in the test of H. Shay, D. Sun and H. Greenstein, Gastorenterology 1954, 26, 906-13. Compounds which exhibit activity in the above anti-ulcer or anti-secretory tests are regarded as anti-ulcer agents.

The compounds of formula I may be prepared by various methods all of which are included in the invention.

A general method of preparing the compounds of formula I comprises treating a corresponding compound in which X is hydrogen by known methods to introduce the desired group X.

Compounds of formula I wherein X is $CSNHR^3$ are usually prepared from the corresponding amides of formula 2 wherein X is $CONHR^3$ or nitriles of formula I wherein X is CN. These in turn may be prepared from the corresponding esters of formula I wherein X is $CO_2R^5$.

A method for preparing compounds of formula I in which X is $CO_2R^5$ and $R^5$ is hydrogen, alkyl of 1-6 carbon atoms or phenylalkyl wherein the alkyl group has 1 to 6 carbon atoms comprises carboxylating a corresponding compound wherein X is hydrogen, to obtain a compound of formula I in which X is COOH or a metal salt thereof, and if desired esterifying the product with an hydroxyl compound $R^5OH$, wherein $R^5$ is alkyl of 1–6 carbon atoms or phenylalkyl wherein the alkyl portion has 1-6 carbon atoms. The carboxylation may be achieved by preparation of a metal salt of compound of formula I wherein X is COOH, by treating a corresponding compound in which X is hydrogen, with a metal alkyl, followed by treatment of the product is situ with carbon dioxide, conveniently by bubbling $CO_2$ gas into the reaction mixture. The compound of formula I in which X is $CO_2H$ is obtained by treatment of the product, a metal salt of a compound of formula I in which X is COOH, with acid e.g. hydrochloric or hydrobromic acid. A convenient method is to treat a solution of the salt with gaseous hydrogen chloride. The metal alkyl may be one of a monovalent metal e.g. $MR^{10}$ wherein M is sodium, potassium or lithium and $R^{10}$ is alkyl, aryl or aralkyl or one of a divalent metal $M(R^{10})_2$ wherein M is calcium or magnesium. A convenient reagent $MR^{10}$ is lithium phenyl or n-butyl lithium.

When a compound of formula I in which $R^1$ is methyl and $R^2$, $R^6$ and $R^7$ are hydrogen and X is hydrogen is carboxylated, the carboxylation may occur either on the methyl group $R^1$ or at the desired X position. If a mixture of desired and undesired product is formed the desired product can be separated during subsequent work-up.

The esterification of a compound of formula I in which X is $CO_2H$ may be carried out using an hydroxyl commpound $R^5OH$, wherein $R^5$ is as alkyl or phenylalkyl according to standard procedures, e.g. in the presence of an acid catalyst e.g. some concentrated sulphuric acid or after saturation with hydrogen chloride gas or a Lewis acid e.g. boron trifluoride if desired with heat or treatment of the silver salt, (X is COOAg) with an iodide $R^5I$ wherein $R^5$ is as defined above.

The yield of ester can be improved by introducing a further quantity of the metal alkyl after the $CO_2$ treatment, followed by a further amount of $CO_2$. It is believed that the further quantity of metal alkyl and $CO_2$ gives the bis acid metal salt of formula IV

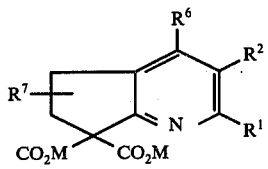
(IV)

wherein $R^1$, $R^2$, $R^6$ and $R^7$ are as defined in connection with formula I and M is the metal of the metal alkyl e.g. sodium, potassium or lithium, and this salt spontaneously decarboxylates during the esterification.

A further method for preparing esters of formula I wherein X is $CO_2R^5$ comprises treating a compound of formula I as defined above wherein X is a hydrogen atom with a metal alkyl (as defined above) and then treating the product with a haloformate of formula $HalCOOR^5$ wherein Hal is a halogen atom e.g. chlorine or bromine and $R^5$ is as defined above. The product is usually a mixture of the desired compound of formula I wherein X is $CO_2R^5$ and the corresponding bis-ester of formula V

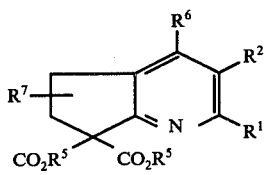
(V)

These bis-esters are useful for preparing the corresponding compounds of formula I wherein X is $CO_2H$. This mixture of mono and bis esters can be converted directly to the corresponding compound of formula I where X is $CO_2H$, by saponification with an alkali or alkaline earth metal hydroxide to give a mixture of the metal salt of the mono acid of formula I wherein X is $CO_2H$ and the metal salt of the diacid of formula V wherein $R^5$ is H. Treatment of this mixture with mineral acid e.g. hydrochloric acid gives the desired acid of formula I wherein X is $CO_2H$ since the diacid spontaneously decarboxylates to form the mono acid.

The product of the haloformate reaction may be treated with a further quantity of the metal alkyl followed by a further quantity of the haloformate thereby producing more of the bis ester (V).

A further method for preparing compounds of formula I in which X is $CO_2H$ comprises decarboxylation of a compound of formula V

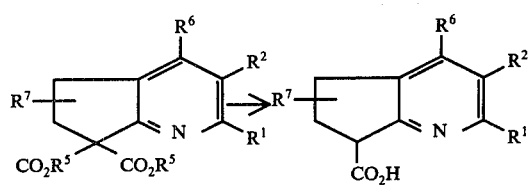

wherein $R^1$, $R^2$, $R^5$ are as previously defined. The decarboxylation can be carried out by heating the dicarboxylic acid of formula V wherein $R^5$ is hydrogen.

Usually the dicarboxylic acid is prepared in situ by hydrolysis of the corresponding di-ester, wherein $R^5$ is as defined above except hydrogen. The hydrolysis and decarboxylation may be carried out by heating with a dilute mineral acid e.g. HCl or sulphuric acid or the diester may be saponified with alkali e.g. sodium or potassium hydroxide. The resulting salt is then acidified and decarboxylated by heating Compounds of formula I, in which X is $CONHR^3$ may be prepared by treatment of a corresponding compound of formula I wherein X is COCl or $CO_2R^5$ and $R^5$ is as defined above, except hydrogen, with ammonia to give a compound of formula I in which X is $CONH_2$, which may be subsequently alkylated to introduce the group $R^3$ wherein $R^3$ is as defined above except hydrogen. Conveniently a compound of formula I wherein X is $CO_2R^5$ wherein $R^5$ is lower alkyl, especially methyl or ethyl, is treated with ammonia. Alternatively substituted amides of formula I wherein X is $CONHR^3$ and $R^3$ is other than hydrogen may be prepared by treatment of the carboxylic ester of formula I wherein X is $CO_2R^5$ and $R^5$ is other than hydrogen with an amine of formula $R^3NH_2$ wherein $R^3$ is as defined previously except hydrogen. The substituted amides may conveniently be prepared from the acid chloride of formula I wherein X is COCl by treatment with a primary amine $R^3NH_2$.

An example of a primary amine which may be used in the above reactions is methylamine.

The acid chlorides may be prepared by treatment of the corresponding acid of formula I, wherein X is $CO_2H$ with thionyl chloride, phosphorus oxychloride or phosphorus pentachloride.

A further process for preparing compounds of formula I as defined above wherein $R^1$ and $R^2$ are as defined above and X is $CONHR^3$ wherein $R^3$ is hydrogen or alkyl, comprises treating an ester compound of formula I, wherein X is $CO_2R^5$ and $R^5$ is alkyl with an amide of formula $R^9CONHR^3$ or a salt thereof wherein $R^3$ is hydrogen or alkyl and $R^9$ is hydrogen or lower alkyl in the presence of an alkali-metal alkoxide.

Preferably a molar equivalent of alkali-metal alkoxide is used for each mole of ester of formula I. The alkali-metal alkoxide may be one derived from a lower alkanol having from 1 to 6 carbon atoms e.g. methanol or ethanol. The alkali-metal is preferably sodium.

The ester of formula I is preferably a lower alkyl ester.

The amide $R^9CONHR^3$ is preferably one in which $R^9$ is hydrogen or methyl. $R^3$ is also preferably hydrogen or methyl. Thus preferred amides are formamide, N-methylformamide, acetamide and N-methylacetamide. Salts, especially alkali-metal salts of these amides may be used as starting materials.

The reaction may be carried out by heating the reactants together.

The amides of formula I, wherein X is $CONH_2$ may also be prepared by partial hydrolysis of the corresponding nitriles of formula I, wherein X is CN. This hydrolysis may be accomplished in conventional manner e.g. by concentrated (e.g. 96%) sulphuric acid.

Thioamides of formula I wherein X is $CONHR^3$ wherein $R^3$ is as already defined may be prepared by treatment of the corresponding compounds in which X is $CONHR^3$ with $P_2S_5$ e.g. by refluxing in pyridine. As mentioned below when the starting material is one in which X is $CONH_2$, decomposition to the nitrile may occur. We have found that this decomposition can be avoided by conducting the $P_2S_5$ reaction in the presence of $H_2S$. Alternatively the thioamides may be prepared by treatment of a nitrile of formula I, wherein X is CN with $H_2S$ to give the unsubstituted thioamide wherein X is $CSNH_2$. Substituted thioamides may be obtained by conducting this reaction in the presence of a primary amine $R^3NH_2$ wherein $R^3$ is as defined above except hydrogen. The $H_2S$ reaction can be carried out in a suitable solvent in the presence of a catalyst such as a tertiary amine e.g. a trialkyalamine such as triethylamine.

Substituted thioamides may also be prepared by treatment of an unsubstituted thioamides of formula I, wherein X is $CSNH_2$ with an amine of formula $R^3NH_2$ wherein $R^3$ is as previously defined is other than hydrogen, in the presence of $H_2S$. The amine may be a mono alkylamine e.g. methylamine.

The nitriles of formula I wherein X is CN, may be prepared by dehydration of the corresponding emides of formula I wherein X is $CONH_2$. Such dehydration can be carried out with $P_2O_5$ the dehydrating agent. Other dehydrating agents are phosphorus pentachloride or thionyl chloride. It has also been found that this decomposition can be effected with $P_2S_5$ and this is believed to be a novel reaction per se. The decomposition with $P_2S_5$ has been observed as a side reaction during the conversion of the amides of formula I wherein X is $CONH_2$ to the corresponding thioamides wherein X is $CSNH_2$ using $P_2S_5$. The nitrile can either be separated, e.g. by chromatography or the mixture treated with $H_2S$ for conversion of the nitrile to the corresponding thioamide. The dehydration may also be effected by heating the amide in hexamethylphosphorictriamide as solvent. When using this solvent it has been found that a compound of formula I in which X is $CONMe_2$ may be formed as a significant by-product. The latter is also believed to be a novel reaction per se.

A further method for preparing the thioamides of formula I, wherein X is $CSNH_2$ comprises reacting a nitrile of formula I wherein X is CN with a thioamide of formula $R^8CSNH_2$ wherein $R^8$ is an alkyl group, e.g. a loweralkyl group of 1-6 carbon atoms, preferably a methyl group, in a suitable solvent such as dimethyl formamide saturated with hydrogen chloride.

The starting compounds of formula I wherein X is hydrogen, used in the above mentioned carboxylation reaction may be prepared by cyclisation of a compound of formula VI in the presence of hydroxylamine

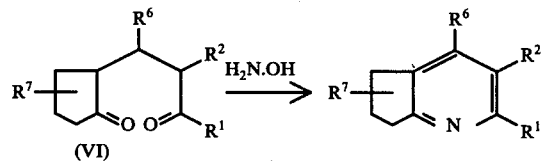

(VI)

wherein $R^1$ and $R^2$ are as defined above but $R^1$ is preferably other than hydrogen and $R^6$ and $R^7$ are as defined above. Starting compounds of formula I, when X is hydrogen, $R^1$ is hydrogen and $R^7$ is hydrogen, or if not hydrogen is not on the 5-position may be prepared by reduction of the corresponding 5-oxo compound (VII) using a reducing agent which does not affect the unsaturation of the fused pyridine ring e.g. hydrazine i.e. a Wolff-Kishner reduction.

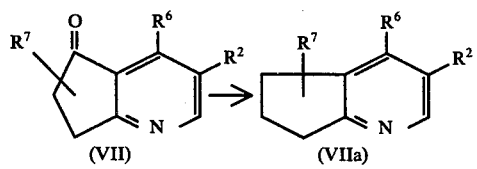

(VII)          (VIIa)

The starting material of formula (VII) wherein $R^2$ and $R^6$ are hydrogen may be prepared by the following scheme:

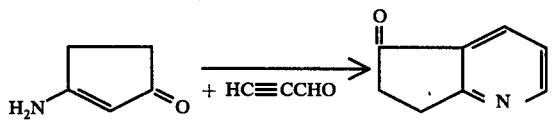

The reaction can be carried out in a suitable solvent e.g. dimethylformamide at room temperature followed by distillation of the products.

Compounds of formula (I) wherein X is hydrogen, $R^1$ is hydrogen and $R^2$ is other than hydrogen may be prepared by known methods.

The compounds of formula VI (wherein $R^7$ is hydrogen or is not on both positions adjacent the oxo group) may be prepared by one of the following schemes:

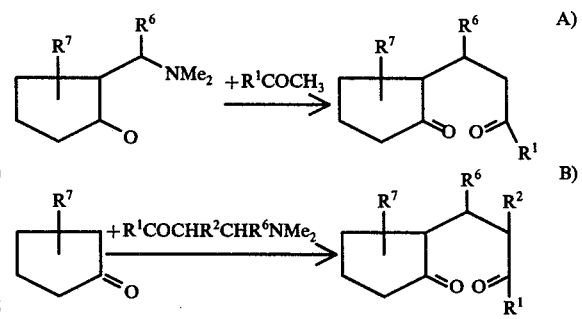

wherein $R^1$, $R^2$, $R^6$ and $R^7$ are as defined above, $R^1$ being other than hydrogen. The reactions used are known compounds or may be prepared by methods known for analogous compounds.

Other compounds for preparing starting compounds of formula I wherein X is hydrogen are described in the literature e.g. Breitmaier & Bayer Tetrahedron letters No. 38, 1970, 3291–3294, which gives methods for preparing compounds in which X is hydrogen and $R^1$ and $R^2$ are hydrogen and X is hydrogen and $R^2$ is alkyl.

Another method for preparing thioamines of formula I, wherein X is $CSNHR^3$ wherein $R^3$ is as defined in connection with formula I, comprises treating a thioester of formula I wherein X is $CSSR^5$ and $R^5$ is alkyl or aralkyl with a compound of formula $R^3NH_2$ wherein $R^3$ is as defined in connection with formula I.

The thioester starting materials may be prepared by treating a compound of formula I wherein X is hydrogen with a metal alkyl $MR^{10}$ or $M(R^{10})_2$ as already discussed above and then treating the product with carbon disulphide to give the metal salt of the thioacid of formula I. This is then treated with an alkyl halide $R^5$Hal wherein $R^5$ is an alkyl or aralkyl group and Hal is chlorine, bromine or iodine.

The invention also includes pharmaceutical compositions comprising a compound of formula I wherein X is $CSNHR^3$ and $R^3$ is as defined in connection with formula I and a pharmaceutical carrier.

For the pharmaceutical carrier any suitable carrier known in the art can be used to prepare the pharmaceutical composition. In such a composition, the carrier may be solid, liquid or mixture of a solid and a liquid. Solid form compositions include powders, tablets and capsules. A solid carrier can be one or more substances which may also act as flavouring agents, lubricants solubilisers, suspending agents, binders or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often by dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate magnesium trisilicate, sodium bicarbonate or the alumina gel described in British specification No. 1,284,394.

Examples 35,45,46,48,49 and 50 illustrate the invention. The remaining examples are included for reference purposes. All temperatures are in ° C.

EXAMPLE 1

(A) 2-Phenyl-5,6,7,8-tetrahydroquinoline 2-(3'-Phenyl-3'-oxopropyl)cyclohexanone was prepared according to the method of W. Hahn and J. Epsztain (Roczniki Chem. 1963, 37, 403–12): A mixture of β-dimethylaminopropiophenone (27 gm.) and cyclohexanone (37.5 g.) were heated at reflux for 5 hours under nitrogen and the solvent removed in vacuo. The residual oil was distilled giving 2-(3'-phenyl-3'-oxopropyl)cyclohexanone (14 g.) which was cyclised to the title compound according to the method of Hahn and Epsztain by dissolving the diketone (12 g.) in ethanol (65 ml.), treating with hydroxylamine hydrochloride (9 g.) and heating under reflux for 1 hour. The cooled reaction mixture was poured onto water (300 ml.), extracted with ether (2 × 50 ml.) and the extract discarded. The qqueous solution was made basic with $K_2CO_3$ and extracted with ether (3 × 50 ml.). The combined ether extracts were dried and the solvent removed in vacuo. The residual oil was distilled to give the title compound as a colourless oil (7 g.) b.p. 134°–8° C/15 mm. Found: C, 85.40; H,7.5; N,6.9%, $C_{15}H_{15}N$ requires: C, 86.00; H, 7.2; N, 6.7%

(B) Methyl-2-phenyl-5,6,7,8-tetrahydroquinoline-8-carboxylate

A solution of 2-phenyl-5,6,7,8-tetrahydroquinoline (20 g.) in ether (50 ml.) was added dropwise over 30 mins. to a preformed ethereal solution of phanyllithium (prepared from bromobenzene (40 g.) and lithium (2.78 g.) in dry ether (160 ml.). The reaction mixture was stirred for 1 hour at room temperature and treated with dry $CO_2$ gas until the colour was discharged. The solvent was removed in vacuo and the residue dissolved in ethanol saturated with dry HCl gas (250 ml.) and the solid filtered and recrystallised from water giving 2-phenyl-5,6,7,8-tetrahydroquinoline-8-carboxylic acid hydrochloride (12 g.). This was dissolved in methanol (200 ml.) and the solution treated with dry HCl gas whilst heating at reflux for 4 hours. The solvent was removed in vacuo and the residue dissolved in water (50 ml.), made basic with 2N NaOH and extracted into chloroform (3 × 100 ml.). The combined extracts were dried, evaporated to dryness and the residual solid recrystallised from petroleum ether giving the title compound as colourless needles (11 g.) mp 75° C. Found: C, 76.8; H, 6.5; N, 5.14; $C_{17}H_{17}NO_2$ requires: C, 76.4; H, 6.4; N, 5.2%.

EXAMPLE 2

2-Phenyl-5,6,7,8-Tetrahydroquinoline-8-carboxamide.

Mathyl-2-phenyl-5,6,7,8-tetrahydroquinoline-8-carboxylate (4 g.) was dissolved in methanol previously saturated with ammonia (90 ml.) and heated in a bomb at 100° C for 4 days. Removal of the solvent in vacuo gave an oily solid which on recrystallisation from ethyl acetate gave the title compound as colourless needles (1.5 g.) mp 145° C. Found: C, 76.4; H, 6.5; N, 11.1% $C_{16}H_{16}N_2O$ requires: C, 76.2; H, 6.4; N, 11.1%.

EXAMPLE 3

2-Phenyl-5,6,7,8-tetrahydroquinoline-8-thiocarboxamide

2-Phenyl-5,6,7,8-tetrahydroquinoline-8-carboxamide (8 g.) was dissolved in pyridine (20 ml.), treated with $P_2S_5$ (5.2 g.) and the mixture heated at reflux temperature for 30 minutes. The solvent was removed in vacuo and the residual oil dissolved in dilute HCl, washed with ether (2 × 50 ml.) and the washings discarded. The aqueous solution was made basic, extracted into chloroform (3 × 50 ml.) and the combined extracts dried and evaporated to dryness. The residual oil was chromatographed on silica gel by elution with chloroform giving 8-cyano-2-phenyl-5,6,7,8-tetrahydroquinoline (1.2 g.) as colourless needles from ether mpt. 100° C. Found: C, 82.0; H, 6.2; N, 11.7% $C_{16}H_{14}N_2$ requires: C, 82.0; H, 6.0; N, 11.9%. Further elution with chloroform gave the title compound (1.1 g.) as colourless needles from ether mpt. 154° C. Found: C, 71.8; H, 6.1; N, 10.2%, $C_{16}H_{16}N_2S$ requires: C, 71.6; H, 6.0; N, 10.4%.

EXAMPLE 4

(A) 5,6,7,8-Tetrahydroquinoline

5-Oxo-5H,6,7,8-trihydroquinoline was prepared according to the method of F. Zymalkawski (Arch. Chem. 1961, 294, 759) by adding propiolaldehyde (16 g.) to a solution of 3-aminocyclohex-2-enene (31 g.) in DMF (150 ml.) over 5 mins. When the exothermic reaction had ceased, the flask was fitted for downward distillation and the reaction mixture heated at 100° C under a vacuum of 15 mm. and the distillate collected and discarded. The temperature was raised to 160°–170° collecting the distillate which was dissolved in dilute HCl (75 ml.) and extracted with ether (2 × 50 ml.) The combined ethereal extracts were discarded. The aqueous solution was made basic and extracted with ether (3 × 150 ml.) and the combined ethereal extracts dried and evaporated in vacuo. The residual oil was distilled giving 5-oxo-5H-6,7,8-trihydroquinoline (21 g.) b.p. 133°–4° C/15 mm. which was dissolved in diethylene glycol (190 ml.) and treated with hydrazine hydrate (14 g.) and sodium hydroxide (14 g.). The reaction mixture was heated at reflux for 30 minutes and then for 3½ hours under a Dean and Stark water separator. The cooled reaction mixture was poured onto water (100 ml.), extracted with ether (3 × 100 ml.) and the combined extracts dried and evaporated in vacuo. The residual oil was distilled giving the title compound as a colourless oil (10 g.) b.p. 100°–5° C/15 mm.

(B) Methyl-5,6,7,8-tetrahydroquinoline-8-carboxylate

A solution of 5,6,7,8-tetrahydroquinoline (14 g.) in dry ether (100 ml.) was added dropwise over ½ hour to an ethereal solution of phenyl lithium (prepared from bromobenzene (42 g.) and lithium (3.7 g.) in dry ether (300 ml.) and the reaction mixture stirred at room temperature for a further 1 hour. The cooled reaction mixture was saturated with dry $CO_2$ gas, evaporated in vacuo and the residue treated with methanol previously saturated with dry HCl (500 ml.) and the solution heated at reflux for 12 hours. The solvent was removed in vacuo and the residue dissolved in water (50 ml.), extracted with ether (3 × 150 ml.) and the extracts discarded. The aqueous solution was made basic and extracted with ether (3 × 100 ml.). The combined ethereal extracts were dried, evaporated in vacuo and the residual oil distilled giving methyl-5,6,7,8-tetrahydroquinoline-8-carboxylate as a colourless oil (13 g.) b.p. 92° C/0.05 mm. The hydrochloride was prepared by saturating an ethereal solution with dry HCl gas and recrystallising the resultant solid from methanol-ether to give the hydrochloride of the title compound as colourless needles mpt. 173° C. Found: C, 58.2; H, 6.3; N, 6.3%. $C_{11}H_{13}NO_2.HCl$ requires C, 58.0; H, 6.2; N, 6.2%.

EXAMPLE 5

5,6,7,8-Tetrahydroquinoline-8-carboxamide

Methyl-5,6,7,8-tetrahydroquinoline-8-carboxylate (9 g.) was dissolved in methanol previously saturated with ammonia (270 ml.) and heated in a bomb at 100° C for 5 days. The solvent was removed and the residual oil triturated with hot petroleum ether (40°–60°). The resultant solid was filtered and then recrystallised from ethylacetate giving the title compound as colourless needles mpt. 132° C (5 g.). Found: C, 67.7; H, 7.1; N, 16.0% $C_{10}H_{12}N_2O$ requires: C, 68.1; H, 6.9; N, 15.9%.

EXAMPLE 6

5,6,7,8-Tetrahydroquinoline-8-thiocarboxamide

A solution of 5,6,7,8-tetrahydroquinoline-8-carboxamide (1.2 g.) in pyridine (15 ml.) was treated with $P_2S_5$ (0.8 g.) and the mixture heated at reflux for 30 mins. The solvent was removed in vacuo and the residual oil treated with 2N NaOH (5 ml.) and saturated with solid $K_2CO_3$ and extracted into chloroform (3 × 50 ml.). The combined extracts were dried and the solvent removed in vacuo. The residual oil was dissolved in pyridine (4 ml.) and triethylamine (1 ml.) and the solution saturated with $H_2S$ (6 hours) and allowed to stand overnight. Removal of the solvent gave a solid (850 mgs.) which was recrystallised from methanol giving the title compound as the quarter hyrate, colourless needles m.p. 160° C. Found: C, 59.8; H, 6.2; N, 14.0%. $C_{10}H_{12}N_2S.1/4\ H_2O$ requires: C, 59.6; H, 6.4; N, 13.9%.

The UV, IR and NMR Spectra of the title compound were determined:

1. UV Spectrum in 95% EtOH (1.07 mg. in 100 ml.)
   Max 272 nm, ε13,300
2. IR Spectrum
   $3230\ cm^{-1}$
   $3060\ cm^{-1}$ } $NH_2$ stretch
   $1660\ cm^{-1}$ —$NH_2$ deformation or/and C=CN stretch
   $1575\ cm^{-1}$ C=C stretch -continued

| | | | |
|---|---|---|---|
| 1500–900 cm$^{-1}$ | 'fingerprint region'; numerous bands caused by complex and coupled vibrations. Two bands are particularly prominent 1280 cm$^{-1}$ and 1020 cm$^{-1}$ | | |
| 802 cm$^{-1}$ 720 cm$^{-1}$ | —CH deformation, characteristic of 2,3-disubstituted pyridine. | | |

3. NMR Spectrum - in d$_6$ DMSO (100 MH$_2$)

| | | | |
|---|---|---|---|
| δ 1.5 – 2.3 | broad multiplet | 4 protons | CH$_2$ -6 and 7 |
| δ 2.7 | multiplet | 2 protons | CH$_2$ -5 |
| δ 4.15 | triplet (J=7Hz) | 1 proton | CH-8 |
| δ 7.08 | quartet | 1 proton | H-3 |
| δ 7.44 | quartet | 1 proton | H-4 |
| δ 8.29 | quartet | 1 proton | H-2 |
| δ 9.25 and 9.45 | broad doublet | 2 protons | NH$_2$ |

Coupling constants = J$_{23}$ = 5Hz, J$_{24}$ = 1.5 Hz, J$_{34}$ = 8 Hz

It is indicated in the index to Chemical Abstracts that 5,6,7,8-tetrahydroquinoline-8-thiocarboxamide is disclosed in Z. Naturforch. 6b, 147–155 (1951), however, the actual abstract does not disclose the compound and examination of the paper reveals that the index is in error since the compound actually disclosed is 8-quinoline thiocarboxamide, the benzene ring of which has been shown without the unsaturation being marked in accordance with a custom then in use, see Organic Chemistry, Paul Karrer, 4th English Edition, Elsevier, 1950 eg. at page 813.

EXAMPLE 7

3-Methyl-5,6,7,8-tetrahydroquinoline

The title compound was prepared from commercially available 3-amino-2-methylacrolein and cyclohexanone according to the method of Breitmaier and Bayer (Tet. Letts, 1970, 38, 3291-4) and isolated as a pale yellow oil b.p. 120°/15 mm. (30% yield).

EXAMPLE 8

Methyl 3-methyl-5,6,7,8-tetrahydroquinoline-8-carboxylate

The title compound was prepared from 3-methyl-5,6,7,8-tetrahydroquinoline according to the general method described in Example 1B and isolated as a pale yellow oil b.p. 120°/0.25 mm. (80% yield). The hydrochloride was prepared in the usual way (of Example 6B) and isolated as colourless needles from ethanol/ether m.p. 146° (Found: C, 59.9; H, 6.7; N, 6.0 C$_{12}$H$_{15}$NO$_2$HCl requires: C, 59.60; H, 6.7; N, 5.8%).

EXAMPLE 9

3-Methyl-5,6,7,8-tetrahydroquinoline-8-carboximide

The title compound was prepared from methyl 3-methyl-5,6,7,8-tetrahydroquinoline-8-carboxylate by the method described in Example 2 and was isolated as colourless needles from hexane m.p. 118° (50% yield) (Found: 69.60; H, 7.5; N, 14.8; C$_{11}$H$_{14}$N$_2$O requires: C, 69.5; H, 7.4; N, 14.7%).

EXAMPLE 10

3-Methyl-5,6,7,8-tetrahydroquinoline-8-thiocarboxamide

3-Methyl-5,6,7,8-tetrahydroquinoline-8-carboxamide was treated with P$_2$S$_5$ to give 3-methyl-8-cyano-5,6,7,8-tetrahydroquinoline which was treated with H$_2$S as described in Example 8 giving the title compound as colourless needles from benzene m.p. 151° (50% yield) (Found: C, 63.71; H, 6.85; N, 13.38% C$_{11}$H$_{14}$N$_2$S requires: C, 64.94; H, 6.84; H, 13.58%).

The hydrochloride was prepared by dissolving the title compound in the minimum amount of isopropanol and then adding a solution of ether saturated with dry HCl gas. The hydrochloride precipitated as colourless needles m.p. 219° (Found: C, 54.33; H, 6.23; N, 11.42% C$_{11}$H$_{15}$N$_2$SCl requires: C, 54.42; H, 6.23; N, 11.54%).

EXAMPLE 11

Methyl-3-methyl-5,6,7,8-tetrahydroquinoline-8-carboxaylate n-Butylbromide (285 ml.) in dry ether (500 ml.) was added to clean lithium wire (42 g., 6 m) in dry ether (1 l.) under nitrogen at such a rate to maintain an internal temperature of −15° C. Upon completion of the addition the reaction mixture was stirred until the temperature rose to 10° C (approx. 2 hours). The concentration of butyl lithium was calculated by standardising against N/10 HCl and the quantity of 3-methyl-5,6,7,8-tetrahydroquinoline required in the next stage adjusted to have a 1.2 m excess of butyl lithium.

A stirred solution of 3-methyl-5,6,7,8-tetrahydroquinoline (147 g., 1 m) in dry ether (700 ml.) was treated with a freshly prepared solution of butyl lithium (860 ml. of a 1.4 M solution i.e. 1.2 m) under nitrogen. The reaction mixture was stirred for an additional 15 min. and a slow stream of dry CO$_2$ gas bubbled into the reaction mixture until colourless. The reaction mixture was diluted with water (1.2 l), filtered and the aqueous phase separated and extracted with ether (3 × 500 ml.). The combined ethereal extracts were processed to give recovered 3-methyl-5,6,7,8-tetrahydroquinoline (40 g.) b.p. 116–20°/15 mm.

The aqueous layer was evaporated to dryness and the residual solid treated with a solution of methanol previously saturated with dry HCl gas (1.5 l) and allowed to stand at room temperature for 12 hours. The volatiles were removed in vacuo. The residual oil was redissolved in water (1 l.), extracted with ether (3 × 250 ml.) and the extracts discarded. The aqueous solution was adjusted to pH 9.0 with Na$_2$CO$_3$ and extracted with ether (4 × 250 ml.). The combined extracts were dried and the solvent removed in vacuo to give the title compound as a pale yellow oil (85 g. 42%) GLC (10% SE30, T, = 200°) R$_1$ = 3.25 min, 93% pure.

EXAMPLE 12

3-Methyl-5,6,7,8-tetrahydroquinoline-8-thiocarboxamide

A solution of 3-methyl-5,6,7,8-tetrahydroquinoline-8-carboxamide (27.9 g. 0.14 m) in dry pyridine (300 ml.), saturated with H$_2$S gas, was treated with P$_2$S$_5$ (26 g., 0.14 m) and heated at reflux for 45 min. whilst maintaining a slow stream of H$_2$S gas. The reaction mixture was evaporated to dryness in vacuo and cooled to 0° C, made alkaline with 10% sodium hydroxide and the solution extracted with chloroform (3 × 100 ml.). The combined extracts were washed with brine, dried and evaporated in vacuo. The residual oil was triturated with benzene and the solid filtered and recrystallised from benzene to give the title compound as pale yellow needles m.p. 149° (21.8 g., 87%). The hydrochloride was prepared as already described in Example 10 and isolated as colourless needles m.p. 219° C.

EXAMPLE 13

1,2,3,5,6,7-Hexahydro-dicylopenta[b,e]pyridine-3-thiocarboxamide hydrochloride A mixture of 2-($\beta$-dimethylaminoethyl)cyclopentanone (87 g.) and cyclopentanone (210 g.) was heated at reflux for 12 hours. The excess cyclopentanone was removed by distillation and the residue was dissolved in ethanol (300 ml.) and treated with hydroxylamine hydrochloride (100 g.) and the mixture heated at reflux for 1½ hours. The cooled reaction mixture was dissolved in water (1 liter), washed with ether (3 × 200 ml.) and the aqueous phase adjusted to pH 10.0 with sodium carbonate and extracted with ether (3 × 200 ml.). The combined extracts were dried (MgSO$_4$) and the solvent removed to give a residual oil which was distilled at 0.2 mm to give 1,2,3,5,6,7-hexahydrodicyclopenta [b,e]-pyridine as a colourless oil (50 g.) b.p. 100° C. The pyridine is converted to the methyl 3-carboxylate following the method described in Example 11 and the carboxylate converted to 1,2,3,5,6,7-hexahydro-dicyclopenta[b,e]pyridine-3-carboxamide, by the general method described in Example 9. The carboxamide is isolated as colorless needles from methanol m.p. 188° C. (Found: C, 71.1; H, 7.2; N, 14.3. C$_{12}$H$_{14}$N$_2$O requires: C, 71.3; H, 7.0; N, 13.9%).

The carboxamide (1.9 g.) is converted to the the thioamide by the method described in Example 12 and isolated as a pale yellow solid which is converted to the hydrochloride by treating a solution of the base (600 mg.) in methanol (5 ml.) with excess ethereal hydrogen chloride. The resultant solid is recrystallised from methanol-ether to give the title compound as colourless needles m.p. 299° C. (Found: C, 56.4; H, 6.1; N, 10.8. C$_{12}$H$_{14}$N$_2$S.HCl requires: C, 56.6; H, 5.9; N, 11.0%).

The following Examples illustrates pharmaceutical compositions in accordance with the invention.

EXAMPLE A

| Suspension | % w/v |
|---|---|
| Aluminium hydroxide gel B.P.5% Al$_2$O$_3$ | 80% = 4% Al$_2$O$_3$ |
| Magnesia Magma 12% w/v MgO | 10% |
| 5,6,7,8-tetrahydroquinoline-8-thiocarboxamide | 2.0% |
| Glycerin B.P. | 3.0% |
| Alcohol 60 O.P.* | 0.08% |
| Peppermint oil B.P. | 0.015% |
| Saccharin sodium B.P. | 0.01% |
| Methyl p-hydroxybenzoate sodium salt | 0.1% |
| Propyl p-hydroxybenzoate sodium salt | 0.02% |
| Butyl p-hydroxybenzoate sodium salt | 0.01% |
| Water q.s. ad | 100.00 |

*O.P. denotes overproof. 60 O.P. represents 91% w/v Ethanol/Water.

The above suspension is prepared by the following procedure. Add to the Alumina gel Magnesium Magma followed by the 5,6,7,8-tetrahydroquinoline-8-thiocarboxamide dispersed in glycerin, the peppermint oil dissolved in alcohol, the saccharin sodium dissolved in water, and the p-hydroxybenzoates dissolved in water. Make up to volume with water and stir well. Dose: 5 ml. t.d.s.

EXAMPLE B

| Antacid Tablet (chewable) | | |
|---|---|---|
| Saccharin | 1.0 | mg. |
| Hydrated alumina sucrose powder | 750.0 | mg. |
| 5,6,7,8-Tetrahydroquinoline-8-thiocarboxamide | 100.0 | mg. |

-continued

| Antacid Tablet (chewable) | | |
|---|---|---|
| Mannitol B.P. | 170.0 | mg. |
| Maize starch B.P. dried | 30.0 | mg. |
| Talc. purified B.P. | 28.0 | mg. |
| Magnesium stearate B.P. | 20.0 | mg. |
| Peppermint oil B.P. | 1.0 | mg. |
| | 1100.0 | mg. |

Antacid tablets of the above formulation are prepared by the following procedure.

Triturate peppermint oil with talc (screen 40 mesh). Add the triturate, and other ingredients to a blender and mix thoroughly.

Slug the powder to large hard slugs.

Granulate the slugs through a 14 mesh screen.

Compress the granules on a suitable compression machine to give tablets of the required size.

EXAMPLE C

| Anti-ulcer tablet (without antacid) | mg/tablet | |
|---|---|---|
| 5,6,7,8-Tetrahydroquinoline-8-thiocarboxamide | 100 | mg. |
| Celutab | 147.5 | mg. |
| Mag.Stearate | 2.5 | mg. |
| | 250.0 | mg. |

The tablets are prepared by the following method. Blend the ingredients in a suitable blender. Compress the blended ingredients on a suitable compression machine to form tablets of the above composition.

Celutab is a commercial product comprising 90–2% dextrose. 3–5% maltose remainder higher glucose saccharides. Spray crystallized.

EXAMPLE D

A suspension is prepared as described in Example A but replacing 5,6,7,8-tetrahydroquinoline-8-thiocarboxamide by 3methyl-5,6,7,8-tetrahydroquinoline-8-thiocarboxamide.

EXAMPLE E

An antacid tablet is prepared as described in Example B but replacing 5,6,7,8-tetrahydroquinoline 8-thiocarboxamide by 3-methyl-5,6,7,8-tetrahydroquinoline-8-thiocarboxamide.

EXAMPLE F

An anti-ulcer tablet is prepared as described in Example C but replacing 5,6,7,8-tetrahydroquinoline-8-thiocarboxamide by 3-methyl-5,6,7,8-tetrahydroquinoline-8-thiocarboxamide.

The invention includes a method of treating ulcers in an afflicted host which method comprises administering to said host a compound of formula I as defined above wherein X is CSNHR$^3$ R$^3$ is as defined in connection with formula I.

We claim:

1. A compound of formula I

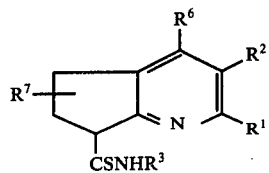

or an acid addition salt thereof with a pharmaceutically acceptable acid, wherein $R^6$ is selected from hydrogen and alkyl containing from 1 to 6 carbon atoms, $R^3$ is hydrogen or alkyl of 1 to 6 carbon atoms, $R^1$ and $R^2$ taken together represent a polymethylene chain of 3 carbon atoms, $R^7$ represents hydrogen or 1 or 2 groups selected from alkyl of 1 to 6 carbon atoms (which may be substituted by alkoxy of 1 to 6 carbon atoms or trifluoromethyl), phenylalkyl wherein the alkyl group has 1 to 6 carbon atoms or phenyl and the phenyl or the phenyl portion of the phenylalkyl group of $R^7$ may be substituted by alkyl of 1 to 6 carbon atoms, lower alkoxy of 1 to 6 carbon atoms, halogen, nitro or trifluoromethyl with the provisio that when two akyl $R^7$ groups are present on the same carbon atom then they are both n-alkyl groups and when two $R^7$ alkyl groups are present on adjacent carbon atoms they are selected from normal and secondary alkyl groups.

2. 1,2,3,5,6,7-hexahydro-dicyclopenta[b,e]3-thiocarboxamide or a pharmaceutically acceptable acid addition salt thereof.

3. A compound as claimed in claim 1, or an acid addition salt thereof with a pharmaceutically acceptable acid wherein $R^6$ and $R^7$ are the same or different and are selected from hydrogen and lower alkyl of 1 to 4 carbon atoms, and $R^3$ is hydrogen or methyl.

* * * * *

UNITED STATES PATENT OFFICE
CERTIFICATE OF CORRECTION

Patent No. 4,085,110     Dated April 18, 1978

Inventor(s)  A.C.W. Curran, R. Crossley & D. G. Hill

It is certified that error appears in the above-identified patent and that said Letters Patent are hereby corrected as shown below:

First page, last line "8 Claims, No Drawings" should read - -3 Claims, No Drawings - - ;

Column 1, line 33 - "1 to 6 atoms" should read - -1 to 6 carbon atoms- - ;

Column 1, line 36 - "from" should read - -form- - ;

Column 2, line 21 - "rece" should read - -race- - ;

Column 2, line 35 - "Gastorenterology" should read - -Gastroenterology- - ;

Column 5, line 39 - "thioamides" should read - -thioamide- - ;

Column 5, line 45 - "emides" should read - -amides- - ;

Column 6, line 55 -     "  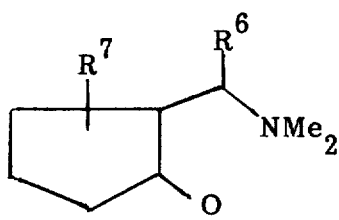  "

should read   -- 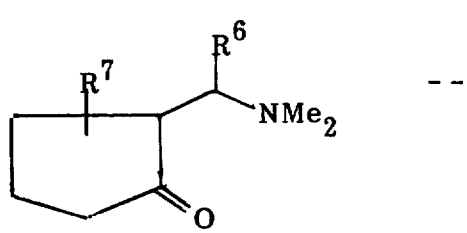 --

UNITED STATES PATENT OFFICE
CERTIFICATE OF CORRECTION

Patent No. 4,085,110                    Dated April 18, 1978

Inventor(s) A.C.W. Curran, R. Crossley & D. G. Hill

It is certified that error appears in the above-identified patent and that said Letters Patent are hereby corrected as shown below:

Column 7, line 9, "thioamines" should read --thioamides--;

Column 7, line 30, "may be solid" should read --may be a solid--;

Column 7, line 58, "often by dissolved" should read --often be dissolved--;

Column 8, line 42, "qqueous" should read --aqueous--;

Column 8, line 55, "phanyllithium" should read --phenyllithium--;

Column 9, line 48, "enene" should read --enone--;

Column 11, line 44, "(of Example 6B)" should read --(cf Example 6B)--;

Column 11, line 68, "C, 64.94" should read --C, 64.04--;

Column 14, line 43 to line 60 should be deleted;

Column 14, line 64, "$CSNHR^3R^3$" should read --$CSNHR^3$ and $R^3$--; and

Column 16, line 10, "1,2,3,5,6,7-hexahydro-dicyclopenta[b,e] 3-thiocar-" should read --1,2,3,5,6,7-hexahydro-dicyclopenta[b,e] pyridine-3-thiocar- --.

Signed and Sealed this

Sixth Day of March 1979

[SEAL]

*Attest:*

RUTH C. MASON
*Attesting Officer*

DONALD W. BANNER
*Commissioner of Patents and Trademarks*